(12) United States Patent
Diamant et al.

(10) Patent No.: US 10,201,846 B2
(45) Date of Patent: Feb. 12, 2019

(54) RETRIEVAL SNARE FOR EXTRACTING FOREIGN OBJECTS FROM BODY CAVITIES AND METHOD FOR MANUFACTURING THEREOF

(71) Applicant: Nordson Corporation, Westlake, OH (US)

(72) Inventors: Valery Diamant, Kazrin (IL); Nadezka Yasko, Tomsk (RU); Kevin L. Delaney, Queensbury, NY (US)

(73) Assignees: Nordson Corporation, Westlake, OH (US); Cook Medical Technologies LLC, Bloomington, IN (US)

(*) Notice: Subject to any disclaimer, the term of this patent is extended or adjusted under 35 U.S.C. 154(b) by 575 days.

(21) Appl. No.: 15/005,163

(22) Filed: Jan. 25, 2016

(65) Prior Publication Data

US 2016/0136720 A1 May 19, 2016

Related U.S. Application Data

(62) Division of application No. 11/866,253, filed on Oct. 2, 2007, now Pat. No. 9,271,746.

(Continued)

(51) Int. Cl.
  *A61B 17/22* (2006.01)
  *B21F 45/00* (2006.01)
  (Continued)

(52) U.S. Cl.
  CPC .......... *B21F 45/008* (2013.01); *A61B 17/221* (2013.01); *A61B 90/39* (2016.02);
  (Continued)

(58) Field of Classification Search
  CPC ................. A61B 17/22; A61B 17/221; A61B 2017/2212; A61B 2017/2215;
  (Continued)

(56) References Cited

U.S. PATENT DOCUMENTS 3,828,790 A 8/1974 Curtiss et al.
3,955,578 A 5/1976 Chamness et al.
(Continued)

FOREIGN PATENT DOCUMENTS

EP   1 273 268 A1   1/2003
EP   1 695 673 A2   8/2006
(Continued)

OTHER PUBLICATIONS

International Search Report—PCT/IB2007/002895 (dated Apr. 9, 2008).

*Primary Examiner* — Bayan Salone
(74) *Attorney, Agent, or Firm* — Baker & Hostetler LLP

(57) ABSTRACT

A retrieval snare for entrapping and retaining a foreign object located in a body and a method for manufacturing of the snare are provided. The snare comprises a structure having a proximal portion and a distal portion and includes a plurality of filaments. The filaments extend from an end of the proximal portion towards the distal portion and return to the end of the proximal portion to form a plurality of loops. The loops are not interconnected at the distal portion, but each side of each loop are connected to a side of an adjacent loop in the proximal portion at more than one point, thereby providing structural rigidity and dilatation ability to the snare.

7 Claims, 9 Drawing Sheets

Related U.S. Application Data

(60) Provisional application No. 60/850,369, filed on Oct. 6, 2006.

(51) Int. Cl.
  *A61B 90/00* (2016.01)
  *A61B 17/221* (2006.01)
  *A61B 17/00* (2006.01)

(52) U.S. Cl.
  CPC .......... *A61B 2017/00526* (2013.01); *A61B 2017/00867* (2013.01); *A61B 2017/2215* (2013.01); *A61B 2017/22035* (2013.01); *A61B 2090/3966* (2016.02); *Y10T 29/49874* (2015.01)

(58) Field of Classification Search
  CPC ........... A61B 2017/22035; A61B 2017/00526; A61B 2017/00867; A61B 19/54; B21F 45/008; Y10T 29/49874
  USPC ...... 29/281.1, 281.5; 269/266; 606/110, 113, 606/114, 127, 128, 159, 191, 200
  See application file for complete search history.

(56) References Cited

U.S. PATENT DOCUMENTS

| | | | |
|---|---|---|---|
| 5,098,440 A | 3/1992 | Hillstead | |
| 5,098,441 A | 3/1992 | Wechler | |
| 5,133,733 A | 6/1992 | Rasmussen et al. | |
| 5,171,233 A | 12/1992 | Amplatz et al. | |
| 5,171,314 A | 12/1992 | Dulebohn | |
| 5,201,741 A | 4/1993 | Dulebohn | |
| 5,387,219 A | 2/1995 | Rappe | |
| 5,522,819 A | 6/1996 | Graves et al. | |
| 5,603,694 A | 2/1997 | Brown et al. | |
| 5,724,989 A | 3/1998 | Dobson | |
| 5,906,622 A | 5/1999 | Lippitt et al. | |
| 5,910,129 A | 6/1999 | Koblish et al. | |
| 5,924,175 A | 7/1999 | Lippitt et al. | |
| 6,066,149 A | 5/2000 | Samson et al. | |
| 6,086,577 A | 7/2000 | Ken et al. | |
| 6,096,034 A | 8/2000 | Kupiecki et al. | |
| 6,099,534 A | 8/2000 | Bates et al. | |
| 6,179,861 B1 | 1/2001 | Khosravi et al. | |
| 6,187,017 B1 | 2/2001 | Gregory, Jr. | |
| 6,191,365 B1 | 2/2001 | Avellanet | |
| 6,193,708 B1 | 2/2001 | Ken et al. | |
| 6,214,025 B1 | 4/2001 | Thistle et al. | |
| 6,217,589 B1 | 4/2001 | McAlister | |
| 6,235,026 B1 | 5/2001 | Smith | |
| 6,245,078 B1 | 6/2001 | Ouchi | |
| 6,278,057 B1 | 8/2001 | Avellanet | |
| 6,280,451 B1 | 8/2001 | Bates et al. | |
| 6,352,539 B1 | 3/2002 | Avellanet | |
| 6,361,540 B1 | 3/2002 | Gauderer et al. | |
| 6,375,661 B2 | 4/2002 | Chu et al. | |
| 6,402,771 B1 | 6/2002 | Palmer et al. | |
| 6,458,139 B1 | 10/2002 | Palmer et al. | |
| 6,458,145 B1 | 10/2002 | Ravenscroft et al. | |
| 6,520,968 B2 | 2/2003 | Bates et al. | |
| 6,554,842 B2 | 4/2003 | Heuser et al. | |
| 6,616,617 B1 | 9/2003 | Ferrera et al. | |
| 6,626,915 B2 | 9/2003 | Leveillee | |
| 6,913,612 B2 | 7/2005 | Palmer et al. | |
| 6,942,673 B2 | 9/2005 | Bates et al. | |
| 7,011,681 B2 | 3/2006 | Vesely | |
| 7,101,380 B2 * | 9/2006 | Khachin | A61B 17/221 |
| 9,039,715 B2 * | 5/2015 | Diamant | A61B 17/22031 606/127 |
| 2001/0049535 A1 | 12/2001 | Leveillee | |
| 2002/0026203 A1 * | 2/2002 | Bates | A61B 17/221 606/127 |
| 2002/0133170 A1 | 9/2002 | Tsuruta | |
| 2003/0018355 A1 | 1/2003 | Goto et al. | |
| 2003/0050663 A1 * | 3/2003 | Khachin | A61B 17/221 606/200 |
| 2003/0130685 A1 | 7/2003 | Daniel et al. | |
| 2003/0135222 A1 | 7/2003 | Baska | |
| 2003/0167052 A1 | 9/2003 | Lee et al. | |
| 2004/0049226 A1 | 3/2004 | Keegan et al. | |
| 2004/0068271 A1 | 4/2004 | McAlister | |
| 2004/0138693 A1 | 7/2004 | Eskuri et al. | |
| 2004/0220608 A1 | 11/2004 | D'Aquanni et al. | |
| 2004/0243174 A1 | 12/2004 | Ackerman et al. | |
| 2005/0021074 A1 | 1/2005 | Elliott | |
| 2005/0033348 A1 | 2/2005 | Sepetka et al. | |
| 2005/0049612 A1 | 3/2005 | Urbanski et al. | |
| 2005/0055045 A1 | 3/2005 | DeVries et al. | |
| 2005/0113845 A1 | 5/2005 | Griego et al. | |
| 2005/0125024 A1 | 6/2005 | Sepetka et al. | |
| 2005/0209634 A1 | 9/2005 | Brady et al. | |
| 2005/0222607 A1 | 10/2005 | Palmer et al. | |
| 2005/0234474 A1 | 10/2005 | DeMello et al. | |
| 2006/0009785 A1 | 1/2006 | Maitland et al. | |
| 2006/0009786 A1 | 1/2006 | Bates et al. | |
| 2008/0086149 A1 * | 4/2008 | Diamant | A61B 17/221 606/113 |

FOREIGN PATENT DOCUMENTS

| | | |
|---|---|---|
| WO | WO 2000/071036 | 11/2000 |
| WO | WO 2004/056275 | 7/2004 |

* cited by examiner

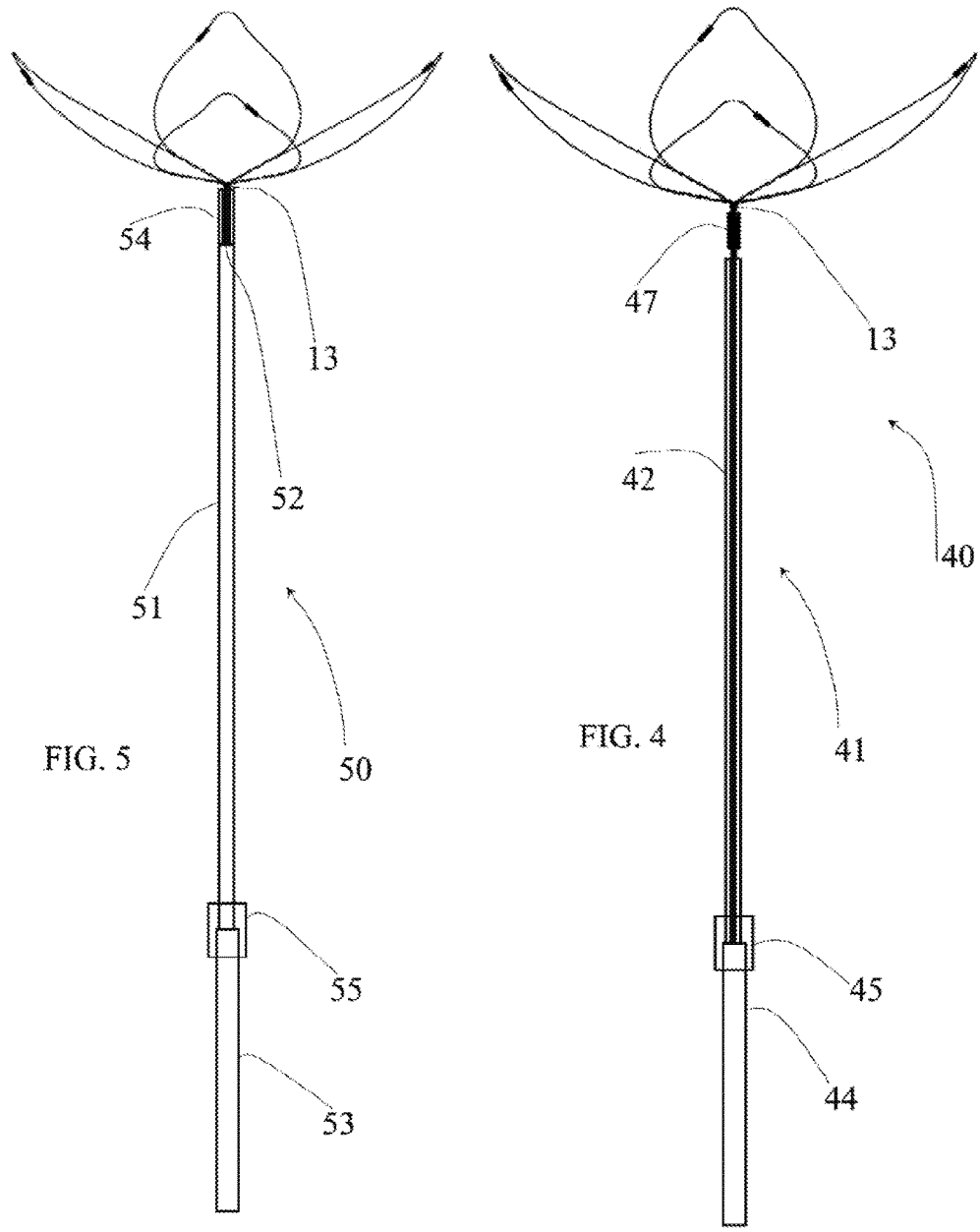

RETRIEVAL SNARE FOR EXTRACTING FOREIGN OBJECTS FROM BODY CAVITIES AND METHOD FOR MANUFACTURING THEREOF

CROSS-REFERENCE TO RELATED APPLICATIONS

This application is a Divisional of U.S. application Ser. No. 11/866,253, filed Oct. 2, 2007 which is related to and claims the benefit of priority to U.S. Provisional Application Ser. No. 60/850,369, filed on Oct. 6, 2006, entitled "RETRIEVAL SNARE FOR EXTRACTING FOREIGN OBJECTS FROM BODY CAVITIES AND METHOD FOR MANUFACTURING THEREOF," the entire contents of which are incorporated herein by reference.

BACKGROUND OF THE INVENTION

Field of the Invention

The present invention relates to an extraction device capable of capturing and releasing objects from hollow bodies, and in particular, to a medical instrument for ensnaring and removing an object from a body.

Background of the Invention

Various instruments are known in the art for removing foreign objects from the body. For example, such instruments are used for removal of stones such as kidney stones, gallstones, and the like from various sites along the urinary tract of a patient's body. Retrieval devices are also widely used for removing foreign articles from the vascular system of a patient. In such a case, examples of the foreign articles include vena cava filters and parts of medical devices, such as catheters, guidewires, cardiac leads, etc., which may break and become detached during medical procedures.

Some types of these instruments employ a retrieval collapsible wire basket arranged within a flexible catheter formed as a tubular sheath adapted to penetrate body passages to reach the location where the object is to be evacuated. Another known type of the retrieval device is a snare configured as a single distal loop which is positioned over a free end of the foreign body, and which is collapsed and tightened around the foreign body.

In an attempt to provide a snare with improved cross sectional vessel coverage, multi loop snares have been developed. These snares include relatively free loops which are not joined at any point between the shaft and the distal ends of the loops. One drawback of many multi-loop snares is that the relative geometry of the free loops is difficult to maintain due to the lack of dilatative strength. These snares are not resistive to forces countering snare opening. Because the relative position of the loops can change, both within a catheter and within a body tract, the loops can actually become displaced and/or entangled, thus preventing the snare to be opened during operation.

BRIEF SUMMARY OF THE INVENTION

There is a need to provide a convenient and safe retrieval snare suitable for the reliable and efficient extraction of foreign objects from body tracts. The present invention satisfies the aforementioned need by providing a retrieval snare suitable for entrapping and retaining a foreign object located in a body for its extraction therefrom. The snare comprises a structure having a petal shape and including a proximal portion and a distal portion. It should be noted that in the description and claims that follow, the terms "proximal" and "distal" are used with reference to the operator of the snare.

The structure is constituted by a plurality of filaments. The filaments extend from an end of the proximal portion towards the distal portion and return to the end to form a plurality of loops. The loops are not interconnected in the distal portion. Each side of each loop is directly connected to a side of an adjacent loop in the proximal portion at more than one point, thereby to provide structural rigidity and dilatation ability to the snare.

According to an embodiment of the invention, the connection of the sides of the loops along the proximal portion is achieved by twisting each pair of the filaments forming the corresponding sides by one or more turns. Preferably, but not mandatory, the twisting is such that the distal connection points of the adjacent loops move from twisted parts of the loops toward the distal portion of the snare when the snare is retracted in a dilator sheath. Thus, when the twisting is formed by at least two turns, an intermediate portion between the proximal portion and the distal portion of the snare is formed. The intermediate portion includes convex cells formed between the distal points and the remaining twisted parts by the corresponding pair of the filaments separated from each other. In turn, when the twisting is formed by only one turn, the convex cells are formed between the end and the distal connection points.

The filaments are bound together at the end of the proximal portion. For example, the filaments at the end of the proximal portion can be bound together by a ferrule. According to an embodiment of the invention, the filaments which are bound together at the end of the proximal portion form a manipulation member.

According to one embodiment of the invention, the filaments are made of non-metallic material. Examples of the non-metallic material include, but are not limited to, Capron, Nylon, etc.

According to another embodiment of the invention, the filaments are made of metallic material. The metallic material can have a thermo-mechanical shape memory characteristic. Moreover, the metallic material can have a superelastic characteristic. Examples of the metallic material include, but are not limited to, NiTi based alloy and stainless steel.

When desired, the metallic material includes a material which provides radiopacity. For example, the material which provides radiopacity is a noble metal. Likewise, the metallic material can be alloyed with one or more of the following metals: palladium (Pd), tungsten (W), niobium (Nb), cobalt (Co), gold (Au), silver (Ag), Tantalum (Ta), and copper (Cu).

According to one embodiment of the invention, the filaments are made of a core tube (cannular strand) containing an axially disposed radiopaque wire.

According to another embodiment of the invention, the filaments are covered by a coating layer. Preferably, but not mandatory, the coating layer is made of a radiopaque material.

According to a further embodiment of the invention, the retrieval snare can include at least one radiopaque marker attached to at least one loop in said distal portion. For example, the radiopaque marker is a ferrule placed around the filament.

According to one embodiment of the invention, the filaments are single-core wires.

According to another embodiment of the invention, the filaments are multiwire strands. For example, the multiwire strands can include a central core wire and at least one another wire twisted about said central core wire. This another wire can, for example, be made of a material having a level of radiopacity greater than the level of radiopacity of the central core wire. For example, this another wire can be made of or include one or more of the following metals: Pt, Au, Pd, W, Nb, Co, Ag, Ta, and Cu.

According to another aspect of the invention, there is provided a retrieval snare apparatus including the snare structure described above and a snare control assembly coupled to the snare structure. The snare control assembly comprises a dilator sheath adapted to penetrate into the body for reaching the object, a manipulator for manipulating the snare for extraction of the object from the body, and a manipulation member arranged within the dilator sheath for connecting the snare to the manipulator. The manipulation member can, for example, be connected to the manipulator through a ferrule placed around the manipulation member and the manipulator. The snare control assembly is configured for retracting the snare within the sheath and protracting the snare therefrom for its opening.

According to one embodiment of the invention, the manipulation member includes at least a part of the plurality of filaments extending from the proximal end towards the manipulator. For example, the manipulation member can include a tube containing these filaments axially disposed within a lumen of the tube along at least a portion of the tube's length.

According to one embodiment of the invention, the filaments extended from the end of the proximal portion towards the manipulator are cut off at a predetermined distance from the end, thereby forming free ends of said plurality of filaments. The manipulation member includes a rod element connected to these free ends, for example, through a ferrule placed and crimped around the rod element and around said free ends. When desired, the ferrule includes a notch configured for facilitation of connection of the rod element to the ferrule by one or more connecting techniques, such as soldering, welding and/or gluing.

Examples of the material from which the manipulation member is made include, but are not limited to, NiTi based alloy, stainless steel and polymer.

According to another aspect of the invention, there is provided a method for manufacturing a novel retrieval snare for entrapping and retaining a foreign object located in a body for its extraction therefrom. According to one embodiment of the invention, the method includes selecting a predetermined number of filaments; and providing a weaving jig having a working surface.

The working surface of the weaving jig has a central portion and a peripheral portion. The working surface has a predetermined convex shape defining an opening angle of the snare, and a predetermined pattern formed by radial channels configured on the surface. At least a part of the radial channels is formed in the form of a plurality of notches extending from a center of the surface towards its periphery. The notches are not interconnected at the peripheral portion of the working surface, but each notch shares a common part with at least one notch of an adjacent radial channel in the central portion of the working surface.

The method further includes placing the filaments into the radial channels to form a plurality of filament loops with free parts of the filaments arranged in the center of the working surface. Then, the filament loops disposed at the peripheral portion of the working surface are fastened to the jig. For example, the fastening of the filament loops to the jig at the peripheral portion of the working surface can be carried out by tying up the filaments by at least one string wound around the jig.

Further, each side of each filament loop disposed in the common part of the radial channels is connected to a side of an adjacent filament loop at more than one point. For example, the connecting of these sides of the filament loops can be achieved by twisting each pair of the filaments forming the corresponding sides.

Further, the method includes temporarily fastening the free parts of the filaments arranged in the center of the working surface together.

Thereafter, the method includes annealing (thermal treatment) of the retrieval snare, thereby to store the snare shape and impart structural rigidity and dilatation ability to the snare. According to an embodiment of the invention, the annealing of the snare includes heating at a temperature in the range of about 400° C.-600° C. over about 10 minutes. It should be understood that generally time of the thermal treatment may be shorter or longer than 10 minutes, depending on the heating technique, jig mass, etc.

For example, the heating can be carried out in a furnace. According to another example, when the filaments are made of electrically conductive material, the heating can be carried out by passing an electric current through the filaments. Depending on the current magnitude, the thermal treatment can be in the range of several seconds to tens of seconds long.

Further, the retrieval snare is cooled; the parts of the filaments tied in the center and at the peripheral portion of the working surface are unfastened; and the jig is removed.

The method also includes the step of binding the free parts of the filaments together. For example, the free parts of the filaments can be bound together by a ferrule.

According to one embodiment of the invention, the structure of the snare can be fabricated from a single length of wire.

According to another embodiment of the invention, the structure of the snare can be fabricated from several wires.

The method of fabrication of the snare can further include forming a manipulation member. The forming of the manipulation member can include twisting the free parts of the filaments.

According to one embodiment of the invention, the forming of the manipulation member includes: providing a tube; cutting off a predetermined number of the free parts of the filaments extended from the proximal end of loops and axially disposing the remaining filaments within a lumen of the tube along at least a portion of the tube's length.

According to another embodiment of the invention, the forming of the manipulation member includes: providing a tube; cutting off all the free parts of the filaments extended from the proximal end of loops at a predetermined distance from a proximal end of the loops; placing free ends of the filaments obtained after cutting into a lumen of the tube; and crimping together the pipe and said free ends of the filaments placed in the tube.

According to a further embodiment of the invention, the forming of the manipulation member includes: providing a rod element; providing a ferrule; cutting off all the free parts of the filaments at a predetermined distance from a proximal end of the loops; connecting free ends of the filaments obtained after cutting to the rod element through the ferrule by placing and crimping the ferrule around the rod element and around the ends of filaments. The ferrule includes a notch configured for facilitation of the connection of the free ends of the filaments to the rod element by at least one connecting technique selected from soldering, welding and gluing.

When desired, the method of snare fabrication further comprises the step of attaching at least one radiopaque marker to at least one filament loop.

According to yet another embodiment of the invention, the method comprises providing a dilator sheath adapted to penetrate into the body for reaching the object; providing a manipulator configured for manipulating the snare for extraction of the object from the body, arranging the manipulation member within the dilator sheath; and connecting the manipulation member to the manipulator. For example, the connecting of the manipulation member to the manipulator can be carried out by placing and crimping a ferrule around the manipulation member and the manipulator.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

Further objects, features and advantages of the invention will become apparent from consideration of the following description and the appended claims when taken in connection with the accompanying drawings.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 10 illustrates a plan view of a distal portion of a retrieval snare in a deployed position, according to another embodiment of the present invention;

FIG. 4 illustrates a schematic view of connection of the loops of the retrieval snare shown in FIG. 1A to a manipulation member, according to one embodiment of the invention;

FIG. 5 illustrates a schematic view of connection of the loops of the retrieval snare shown in FIG. 1A to a manipulation member, according to another embodiment of the invention;

DETAILED DESCRIPTION OF THE INVENTION

Detailed embodiments of the present invention are disclosed herein. It is understood however, that the disclosed embodiments are merely exemplary of the invention and may be embodied in various and alternative forms. The figures are not necessarily to scale; some figures may be exaggerated or minimized to show the details of a particular component. Therefore, specific structural and functional details disclosed herein are not to be interpreted as limiting, but merely as a representative basis for the claims and for teaching one skilled in the art to practice the present invention.

Embodiments of the present invention provide a snare that includes a central structure with a plurality of loops at the distal end of the structure. In order to strengthen the construction, the loops are connected together at joinder length sections located between the distal and proximal ends of the loops to maintain the relative geometry of the loops in both an expanded and compressed condition.

Figure 1A:
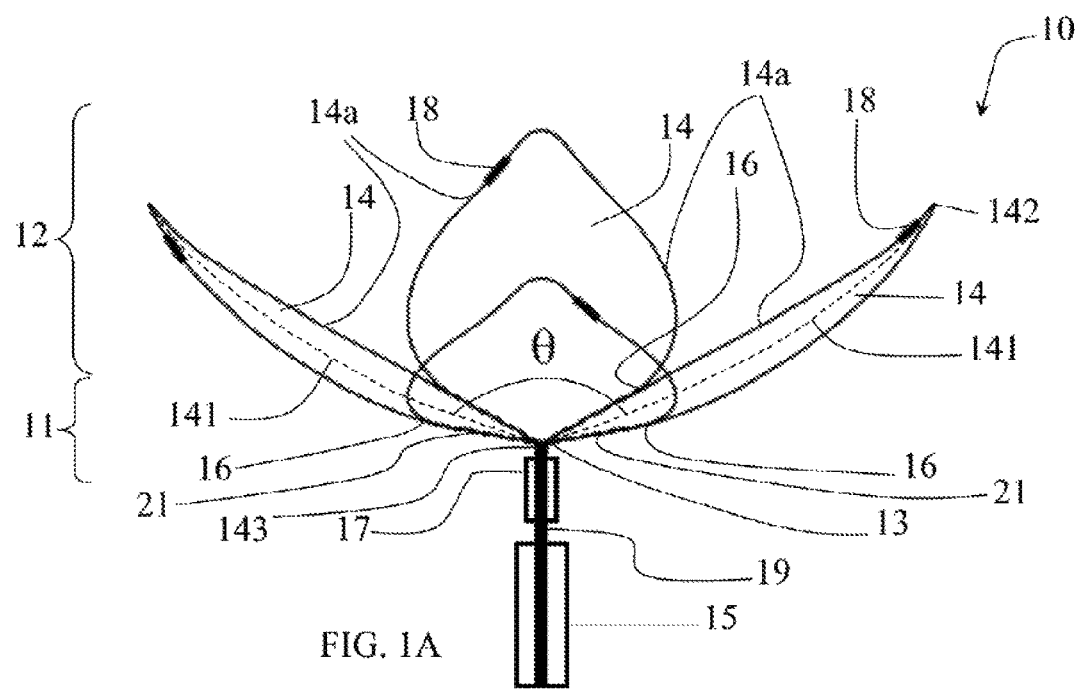
FIGS. 1A and 1B illustrate a plan view and a top view, respectively, of a distal portion of a retrieval snare in a deployed position, according to one embodiment of the present invention.
Figure 1B:
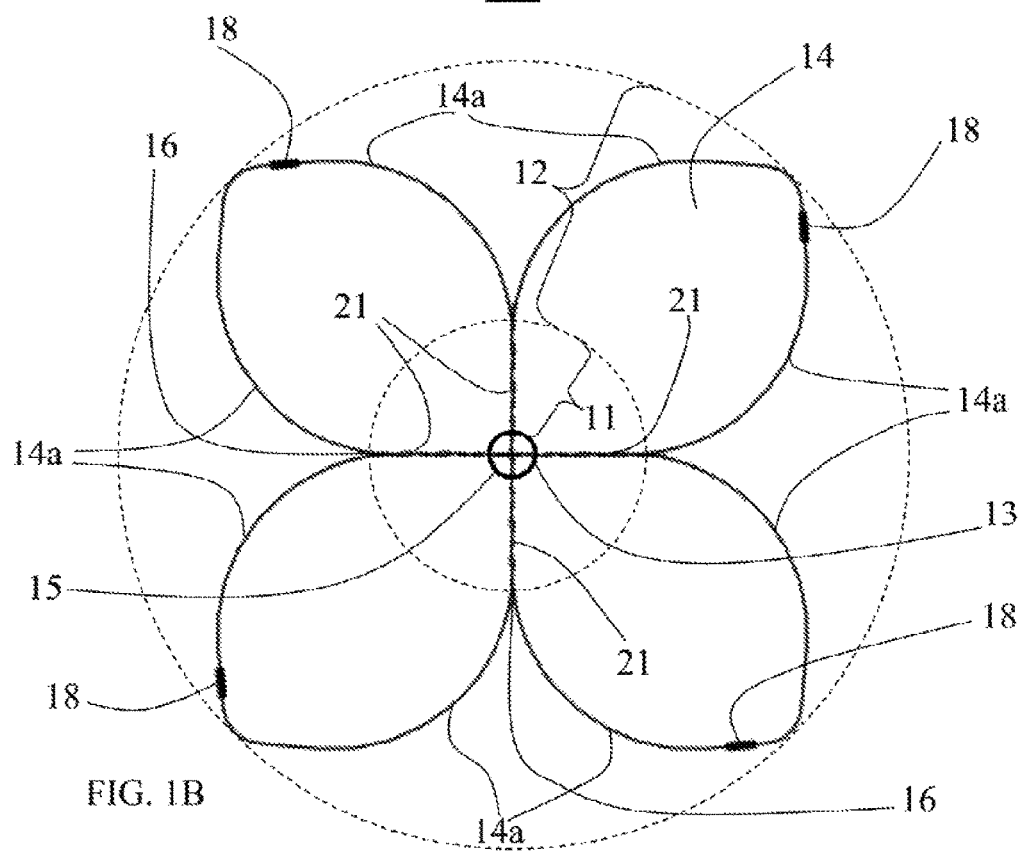

FIGS. 1A and 1B illustrate plan and top views, respectively, of a distal portion of a retrieval snare 10 in a deployed position for entrapping and retaining a foreign object according to one embodiment of the present invention. In general, the structure of the retrieval snare 10 has a petal shape and comprises a proximal portion 11 and a distal portion 12. The structure is formed by a plurality of filaments that extend from an end 13 of the proximal portion 11 towards the distal portion 12 and then return to the end 13 to form a plurality of filament loops 14. In the proximal portion 11, each side 14a of each loop 14 is directly connected to a side 14a of an adjacent loop 14 at continues length sections (i.e., at more than one point) between the end 13 and a distal connection point 16. This feature provides sufficient structural rigidity and dilatation ability to the snare. However, the loops 14 are not interconnected in the distal portion 12. Specifically, the loops 14 deploy radially outward and away from each other in the distal portion 12 when the snare is deployed outside a dilator sheath 15.

The dilator sheath 15 is a thin-walled, cylindrical flexible tube adapted to penetrate into the body for reaching the foreign object. For example, the dilator sheath 15 can be made of a plastic material, such as polyvinyl chloride, NYLON, TEFLON, etc. The dilator sheath 15 can also be made of metal material. For example, it can be made in the form of a coil, (e.g., stainless steel coil) or a metal tube.

When desired, the sheath 15 may be multi-layered with different materials in order to provide a graduated bending and stiffness characteristic over its length.

Figure 1C:
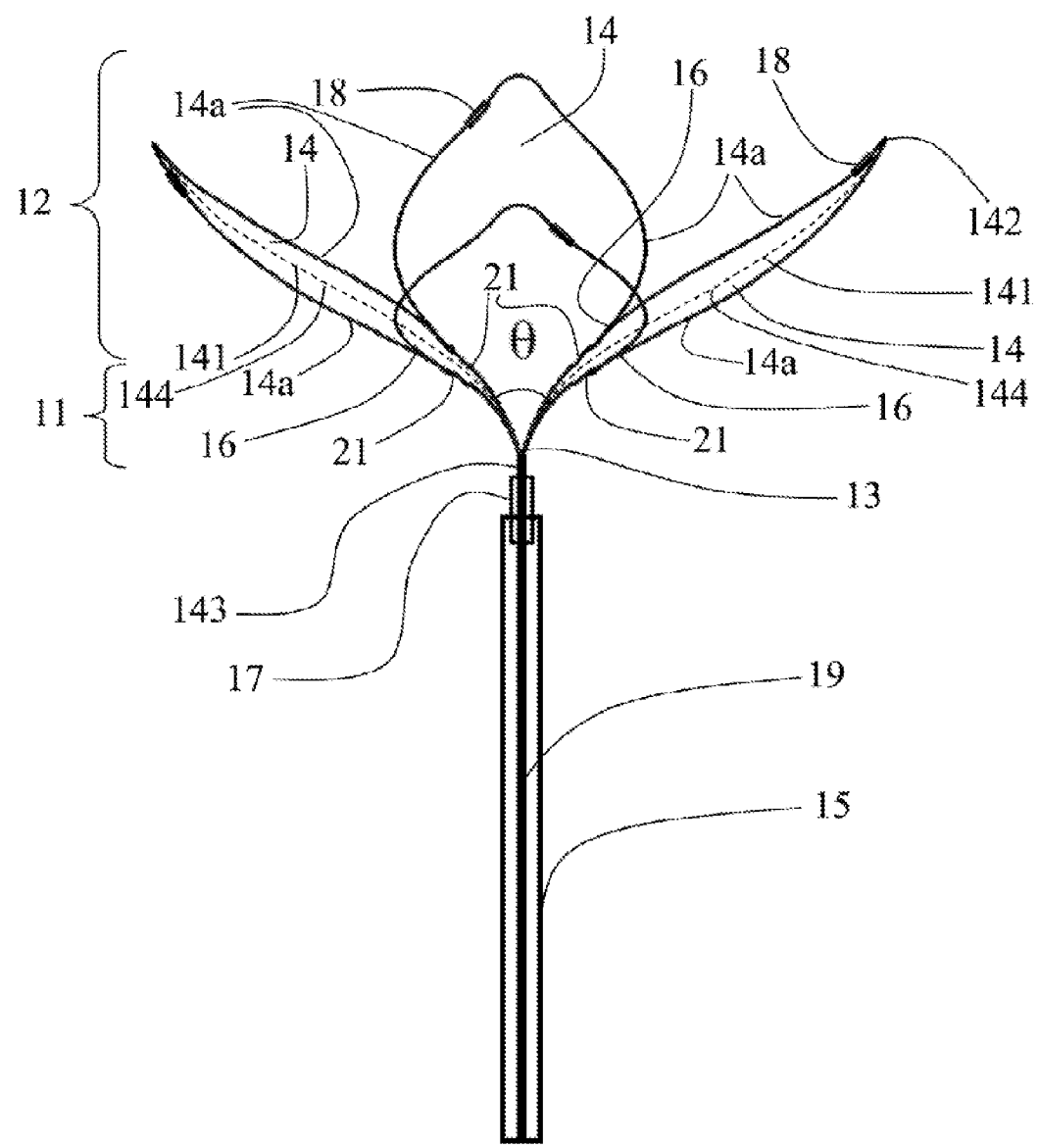

Attention is now drawn to the configuration of the filament loops 14 themselves. According to one embodiment of the invention, the filament loops 14 are generally flat and planar. According to another embodiment of the invention, each side 14a of the filament loops is slightly bent or arcuate, as illustrated in FIG. 1A, into an arc (C-shaped configuration). Such a configuration can enhance the ability to slip the loops over the foreign object and grasp it. According to still another embodiment of the invention, each side 14a of the filament loops is slightly undulated, as illustrated in FIG. 1C, into a somewhat S-shaped configuration. Such a configuration can facilitate retraction of the snare into the sheath 15.

Preferably, an opening angle θ of the deployed snare is in the range of about 10 degrees to about 170 degrees. The effective value of the opening angle depends on the snare application, and is mainly determined by the size of the foreign object. For the purpose of the present invention, when the loops are planar, the opening angle θ can be defined as an angle between planes of the diametrically opposite loops. When the loops are not planar, the opening angle θ can be defined as an angle between various parts of segments 141 connecting a distal end 142, a midpoint 144, and a proximal end 143 of the loops 14. It should be noted that the proximal end 143 of the loops 14 coincides with the end 13 of the proximal portion 11. It should be understood that when the loops are not planar the segments 141 are also bent. Therefore, the value of the angle θ varies along the loop length. In particular, for the configuration when the loops are bent (see FIG. 1A), the value of the angle θ is relatively large near the proximal end 143 and small near the distal end 142. In turn, when the loops are undulated (see FIG. 1C), the value of the angle θ can be relatively small near the proximal end 143, comparatively larger near the midpoint 144 of the loop (i.e. where the loop changes slope), and comparatively smaller adjacent the distal end 142.

It should be understood that although an exemplary snare having four filament loops 14 is illustrated in FIGS. 1A-1C and further drawings, the invention is not limited by such a structure. Generally, any desired number of the loops equal to or greater than two may be utilized.

According to one embodiment of the present invention, the connection of the sides 14a of the loops 14 in the proximal portion 11 is achieved by twisting each pair of the corresponding sides 14a by one or more turns and forming twisted parts 21.

The filaments are bound together at the end 13 of the proximal portion 11. According to an embodiment of the invention, the filaments are bound together by a ferrule 17 crimped or swaged together with the filaments at the end 13 of the proximal portion.

According to another embodiment of the invention, best shown in FIG. 1A, the filaments that extend from the end 13 outside the proximal portion 11 toward a manipulation member 19, are twisted together. Thus, these twisted filaments can possess sufficient stiffness in order to form or be a part of the manipulation member 19 of the snare 10. The manipulation member 19 is arranged within the dilator sheath 15 and operable for retracting the snare within the sheath 15 and protracting the snare therefrom for its opening. The manipulation member 19 connects the snare 10 to a manipulator (not shown) that is operable for manipulating the snare for extraction of the foreign object from the body. According to one embodiment of the invention, the manipulation member 19 is formed from at least a part of the plurality of filaments extending from the end 13 towards the manipulator.

In practice, an operator of the snare can manipulate the manipulation member 19 by means of the manipulator, and thus the snare 10 can be either retracted within the catheter 15 or protracted therefrom. The operator, by holding the manipulator, can also maneuver the catheter 15 within the body organ (not shown), (e.g. to displace it by turning, pushing or pulling).

Referring to FIG. 4, a retrieval snare apparatus 40 is shown which includes at least one of the snares described above and further includes a manipulation member 41 having a tube 42 containing all or at least a part of the plurality of filaments extending from the end 13 towards a manipulator 44. When desired, the filaments can be twisted together to provide additional rigidity to the manipulation member. These filaments are axially disposed within a lumen of the tube 42 along at least a portion of the tube's length. The tube 42 and the filaments can be bound together. For example, the tube and the filaments can be crimped, swaged, glued, soldered or welded together. When desired to increase the surface area binding the filaments to the tube, the tube 42 can have one or more notches (not shown) through which a glue or soldering material can be delivered. In some embodiments, the tube 42 may be disposed within the dilator sheath 15 described above (not shown), thereby forming a snare control assembly.

In another embodiment, the tube 42 may be arranged between a first ferrule 43 and the manipulator 44, as shown in FIG. 4. Alternatively, the tube 42 can bind together the filaments at the end 13 of the proximal portion 11, essentially functioning as the first ferrule 43, and thereby allowing the ferrule 43 to be omitted. The tube 42 can, for example, be made of a metallic material selected from a NiTi based alloy, or stainless steel. Likewise, the tube 42 can be made of a polymer material. According to one example, the manipulation member 41 can be connected to the manipulator 44, for example, through a second ferrule 45 placed and crimped around the tube 42 and the manipulator 44. According to another example, the manipulation member 41 can be directly connected to the manipulator 44, omitting the ferrule 45. Thus, if the manipulator 44 has a cannular end, it can be put on the tube 42 and connected by gluing, soldering and/or welding process. To increase the binding surface, the manipulator 44 can be provided with one or more notches (not shown) through which a glue or soldering material can be delivered.

Referring to FIG. 5, a schematic view of connection of the retrieval snare in FIG. 1A to a tube 51 in order to form a manipulation member 50 of the retrieval snare apparatus is shown, according to another embodiment of the present invention. According to this embodiment, the plurality of filaments extended from the end 13 are cut off at a predetermined distance from the end, thereby forming free ends 52 of the plurality of filaments. These free ends 52 are placed in a lumen of the tube 51 and are crimped or welded together at position 54, thereby to form the manipulation member. The tube 51 of the manipulation member can be connected to a manipulator 53, for example, through a fourth ferrule 55 placed and crimped around the tube and the manipulator 53. According to another example, the manipulation member 50 can be directly connected to the manipulator 53 omitting the ferrule 55. Thus, the manipulator 53 can be put on the tube 42 and connected by gluing, soldering and/or welding process. As discussed above, the manipulator 53 can be provided with one or more notches (not shown) through which a glue or soldering material can be delivered to increase the binding surface area.

Figure 6:
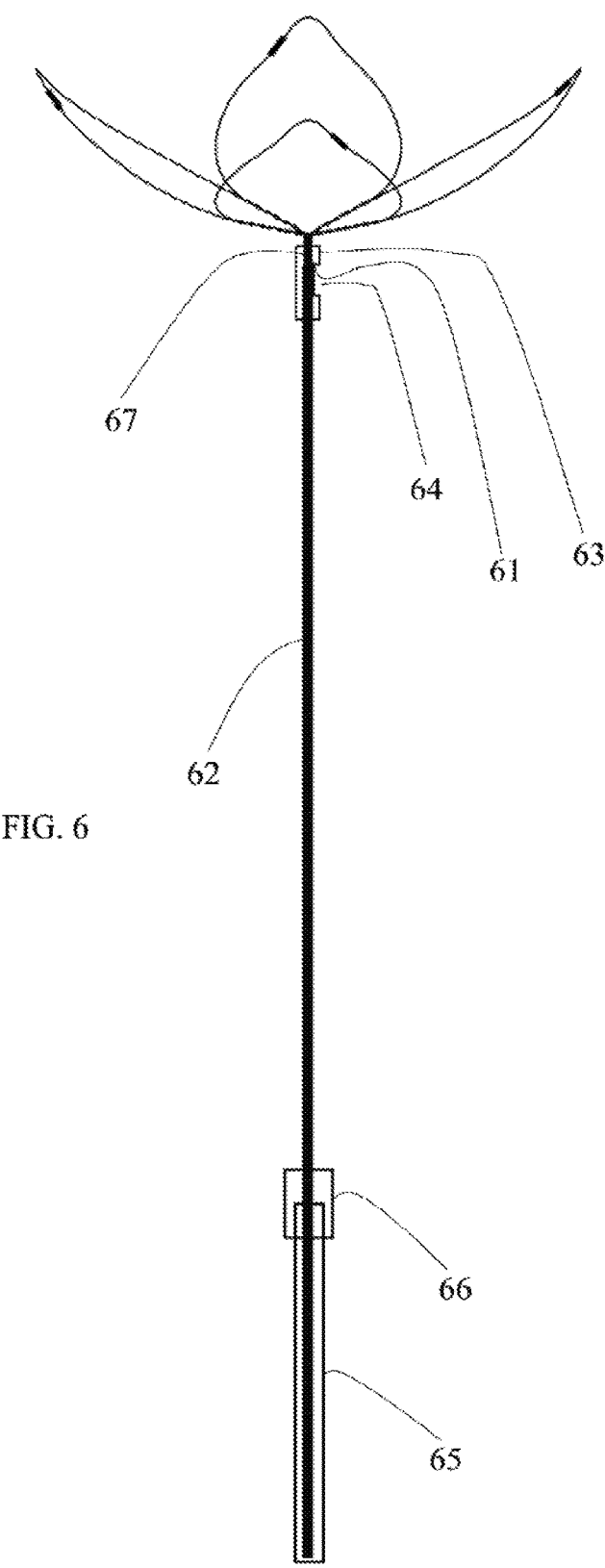
FIG. 6 illustrates a side view of a further embodiment of a manipulation member of the retrieval snare of the invention.

FIG. 6 shows yet another embodiment of a manipulation member of the retrieval snare of the present invention. According to this embodiment, similar to the previous embodiment, the plurality of filaments extending from the end 13 are cut off at a predetermined distance from the end to form free ends 61 of the plurality of filaments. The free ends 61 are connected to a rod element 62. In this case, the rod element 62 is analogous to the manipulation member (41 in FIG. 4).

For example, the connection of the rod element 62 to the free ends 61 of the filaments can be implemented through welding or soldering. Likewise, the connection of the rod element 62 to the free ends 61 of the filaments can be implemented through a fifth ferrule 63 placed and crimped around the rod element 62 and around the free ends. When desired, the fifth ferrule 63 can include a notch 64 configured to facilitate connecting the rod element 62 to the ferrule 63 by at least one connecting technique selected from soldering, welding and gluing.

The rod element 62 can be connected to a manipulator 65, for example, through a sixth ferrule 66 placed and crimped around the rod element 62 and the manipulator 65. As described above, the rod element 62 can also be directly connected to the manipulator 65, for example, by using gluing, soldering or welding process.

The rod element 62 of the manipulation member can, for example, be made of a metallic material, such as a NiTi based alloy or stainless steel. Likewise, the rod element 62 can be made of a polymer material.

According to one embodiment of the invention, each filament is a single-core wire. According to another embodiment of the invention, each filament is a multi-wire strand.

The filaments utilized for the fabrication of the retrieval snare 10 are made of a suitable material that is suitably biocompatible and has thermo-mechanical shape memory and/or superelastic properties. According to one embodiment of the invention, the filaments are made of a metallic material. For example, the metallic material can be selected from a group including a NiTi based alloy (e.g., Nitinol), stainless steel and other materials possessing good shape memory, elastic or superelastic characteristics. According to another embodiment of the invention, the filaments are made of non-metallic material, for example Capron, Nylon, etc.

According to a still further embodiment of the invention, the filaments of the basket are covered by an insulating layer. The insulating layer can, for example, be made of Teflon. The advantage of Teflon is its thermal resistance and low coefficient of mechanical friction, which leads to an additional reduction of traumatism.

A preferable, but not mandatory feature has, the filaments being radiopaque, so as to permit them to be visualized by a fluoroscope with respect to the object to be retracted. Thus, according to one example, radiopacity may be provided by the metallic material from which the filaments are made and may include a material which provides radiopacity, for example a noble metal, such as gold, tantalum, platinum, etc. Likewise, the metallic material can be alloyed with one or more of the following metals: Pd, W, Nb, Co, Ta, and Cu.

According to another example, the filaments are made of a core tube (cannular strand) containing an axially disposed radiopaque wire, for example, a radiopaque core clad with a different outer material. Examples of radiopaque materials include Pt, Au, Pd, W, Nb, Co, Ag, Ta, and Cu without limitation. Examples of cladding materials include stainless steel, Nitinol, and plastics such as Capron and Nylon without limitation.

According to yet another example, the filaments can have radiopaque parts of a predetermined length. These radiopaque parts can form the distal portion (12 in FIG. 1) of the snare or at least a part of the distal portion.

Radiopacity can also be improved through coating processes such as sputtering or plating a radiopaque material onto the filaments, or the snare fabricated from these filaments, thereby to provide a radiopaque coating layer on the filaments.

Likewise, radiopacity can yet be improved by using radiopaque markers which can be attached to or placed around the filaments forming the snare. In this manner, materials which have higher radiopacity than the snare structure itself, such as gold, tantalum or platinum, can be utilized as markers and be strategically placed along the body of the snare to increase the visualization of the snare. For example, the retrieval snare 10 can comprise one or more radiopaque markers (18 in FIG. 1A) attached to or placed around the filaments forming one or more loops (14 in FIG. 1A) in the distal portion (12 in FIG. 1A). For example, the radiopaque marker can be a ferrule put on the filament.

According to another embodiment of the invention, the filaments can be multi-wire strands. In such a case, in order to improve radiopacity, the multi-wire strands can include a central core wire and at least one another wire twisted about said central core wire which is made of a material having a level of radiopacity greater than the level of radiopacity of said central core wire. Examples of such a material include, but are not limited to, Pt, Au, Pd, Ag, Ta, etc.

Figure 2A:
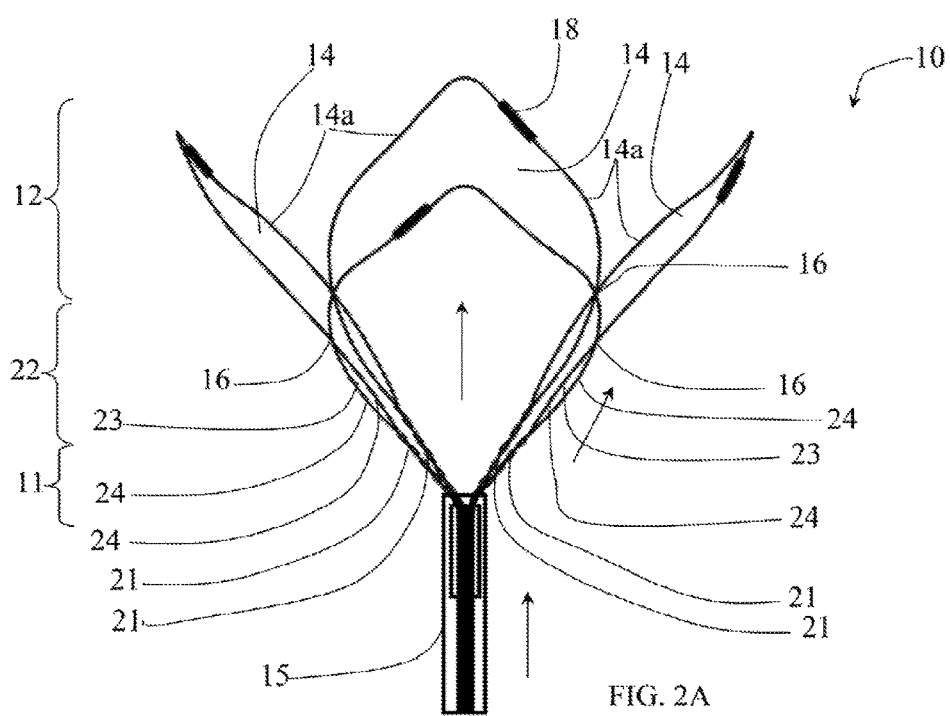
FIGS. 2A and 2B illustrate a plan and a top view, respectively, of the snare shown in FIGS. 1A and 1B in a partially collapsed position when the snare is partially retracted in a dilator sheath.
Figure 2B:
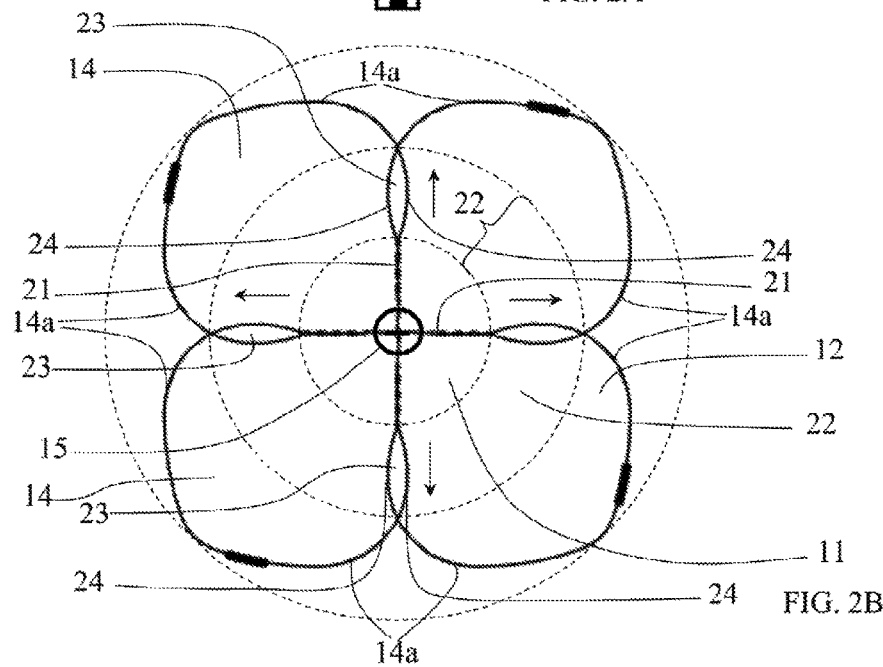

Referring now to FIGS. 2A and 2B, a plan view and a top view are shown, respectively, of the snare shown in FIGS. 1A and 1B in a partially collapsed position when the snare is partially retracted in a dilator sheath. In this case, the opening angle is decreased.

According to the invention, when the sides 14a of the adjacent loops 14 are connected by twisting, the distal connection points 16 of the adjacent loops 14 can slide along the filaments' length when the snare 10 is retracted in the dilator sheath 15. Specifically, when the twisting is formed by two or more turns, the distal connection points 16 can move from the twisted parts 21 of the loops 14 toward the distal portion 12 of the snare, thereby forming an intermediate portion 22 between the proximal portion 11 and the distal portion 12 of the snare 10. The intermediate portion 22 includes convex cells 23 formed between the distal points 16 and the remaining twisted parts 21 by the corresponding pair 24 of the filaments separated from each other. It should be understood that when the twisting is formed by only one turn (not shown), the convex cells are formed between the end 13 of the proximal portion 11 and the distal connection points 16.

Figure 3A:
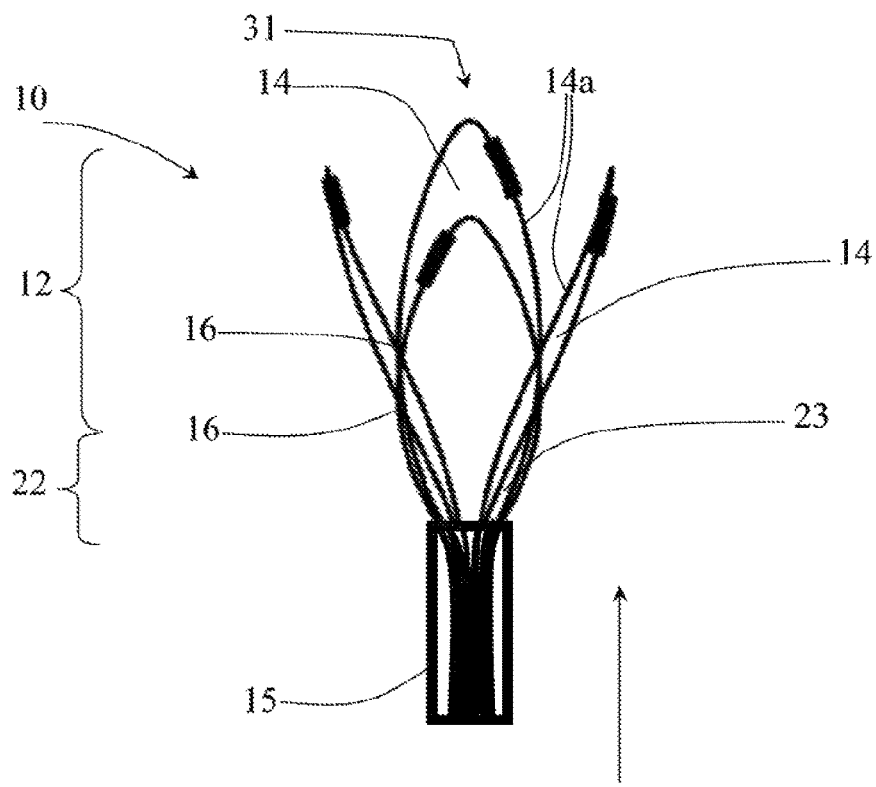
FIGS. 3A and 3B illustrate a side view of the snare shown in FIGS. 2A and 2B during a further retraction in the dilator sheath.
Figure 3B:
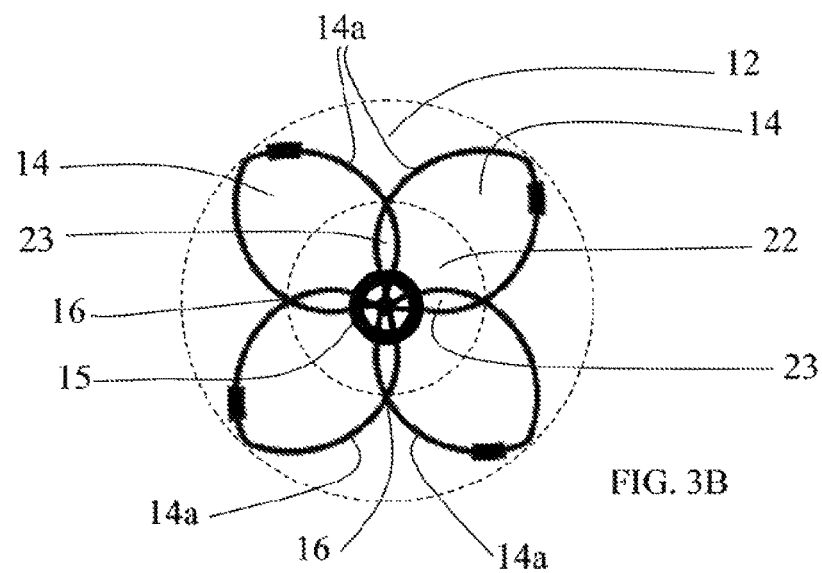

FIGS. 3A and 3B show the snare shown in FIGS. 2A and 2B during a further retraction in the dilator sheath 15. In this case, the proximal portion (11 in FIGS. 2A and 2B) is located in the sheath 15, the distal connection points 16 move further towards a distal end 31 of the snare of the present invention, and the opening angle θ further decreases.

Having explained the structure of the retrieval snare of the present invention, a process of manufacturing the snare will be described hereinbelow.

Figure 7:
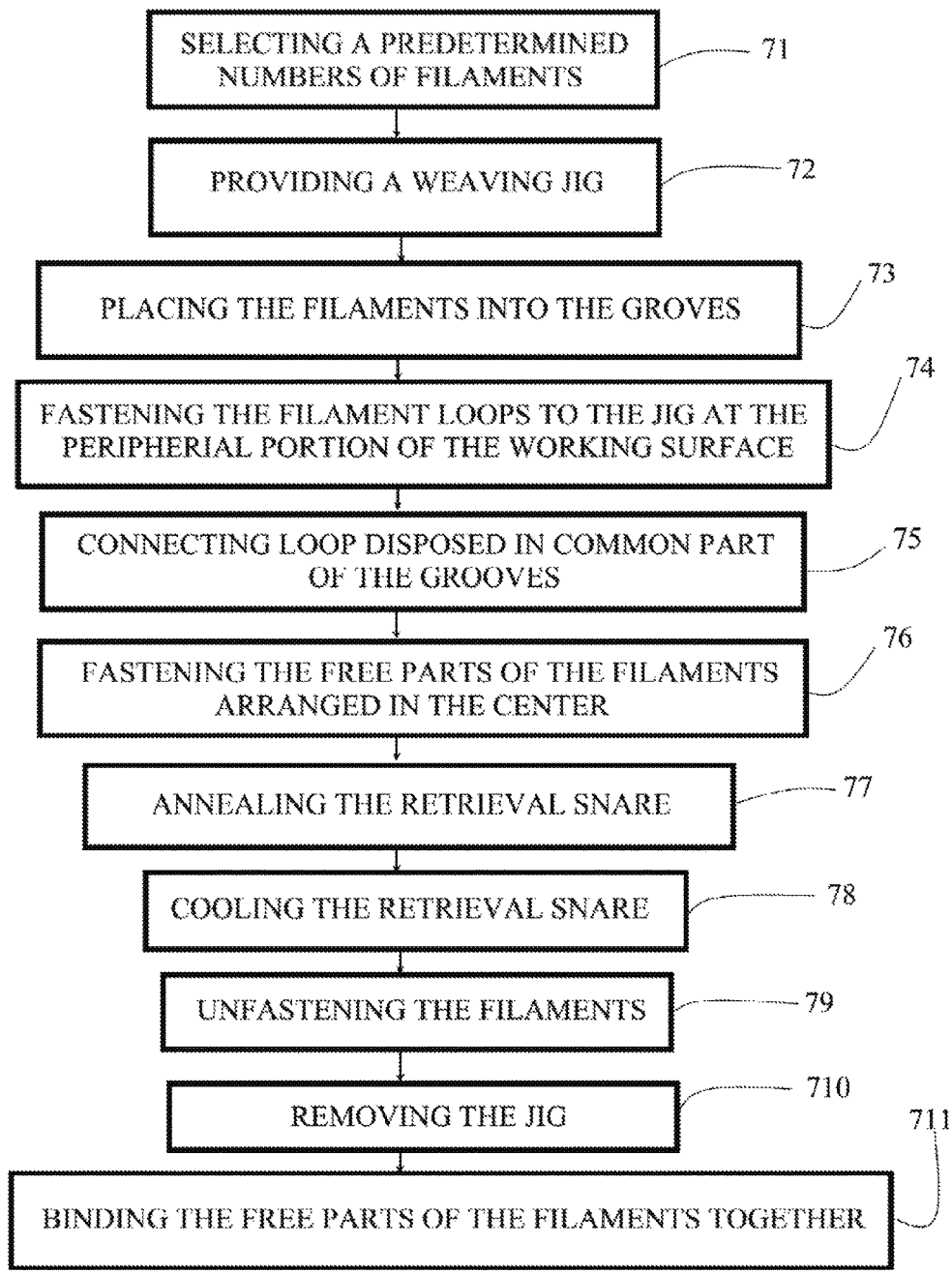
FIG. 7 illustrates a flowchart diagram that describes the method for manufacturing a retrieval snare, in accordance with one embodiment of this invention.

Referring to FIG. 7, the process begins from a step of providing (block 71) of a predetermined number of filaments having predetermined properties, predetermined diameter and length.

According to one non-limiting example of the process, the manufacturing of the retrieval snare is carried out from one length of filament.

According to another non-limiting example of the process the manufacturing of the retrieval snare is carried out from several filaments. In this case, the number of the filaments is equal to the number of the filament loops of the snare.

The filaments selected for the construction of the snare can be single-core wires, or when desired, can be multi-wire strands.

When desired to manufacture a snare with radiopaque characteristics, the filaments can have radiopaque parts of a predetermined length. According to one embodiment of the invention, in order to prepare the filaments with radiopaque parts, the fabrication method can include providing radiopaque coils having the predetermined length, which can be put on a core wire in the desired locations along the wire length. In order to avoid sliding the coils along the core wire, the coils can be welded, soldered and/or glued to the wire. Other method of binding the coils to the core wire can also be utilized. For example, each coil can be fixed on the core wire by means of two ferrules put on and crimped together with the core wire at the two ends of the coil.

According to one embodiment of the invention, in order to prepare the filaments with radiopaque parts, the fabrication method can include providing radiopaque ferrules and placing the ferrules on a core wire and crimping them in the desired locations along the wire length.

After providing the filaments, the process for the fabrication of the retrieval basket includes weaving the retrieval snare from one length of filament or from several filaments.

Figure 8:
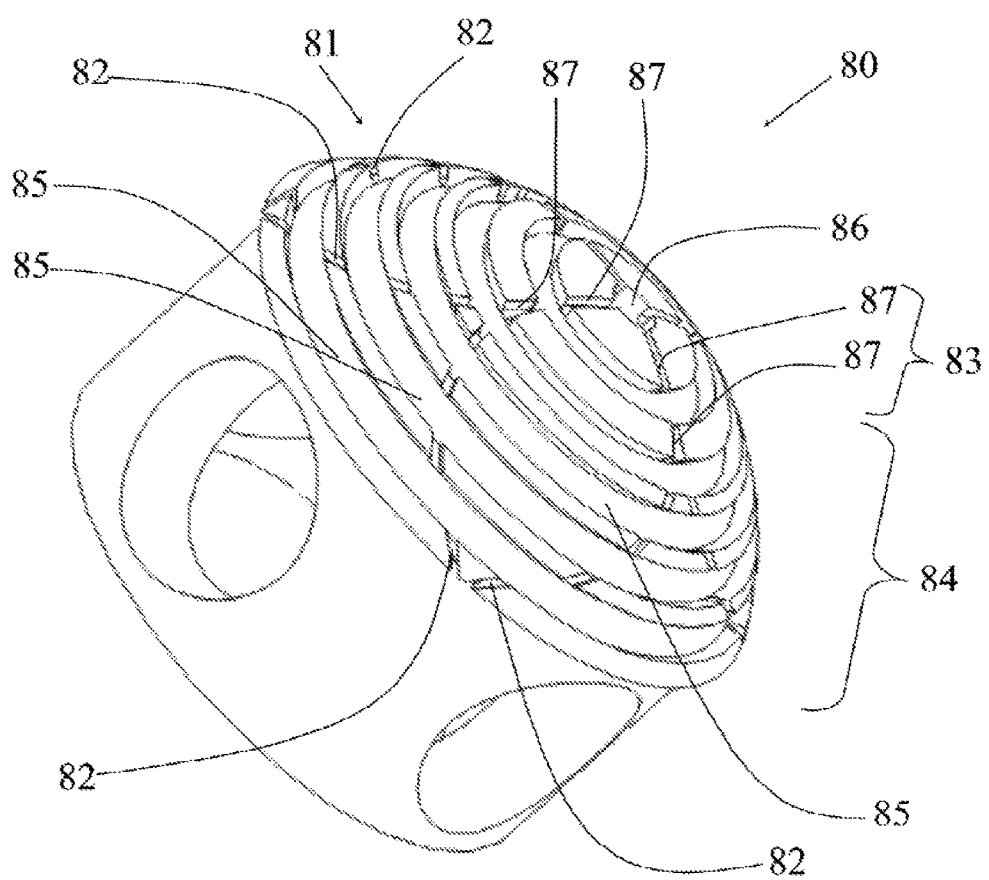
FIGS. 8A and 8B illustrate a perspective and top view, respectively, of an exemplary weaving jig utilized for preparation of a retrieval snare of the present invention.
Figure 8:
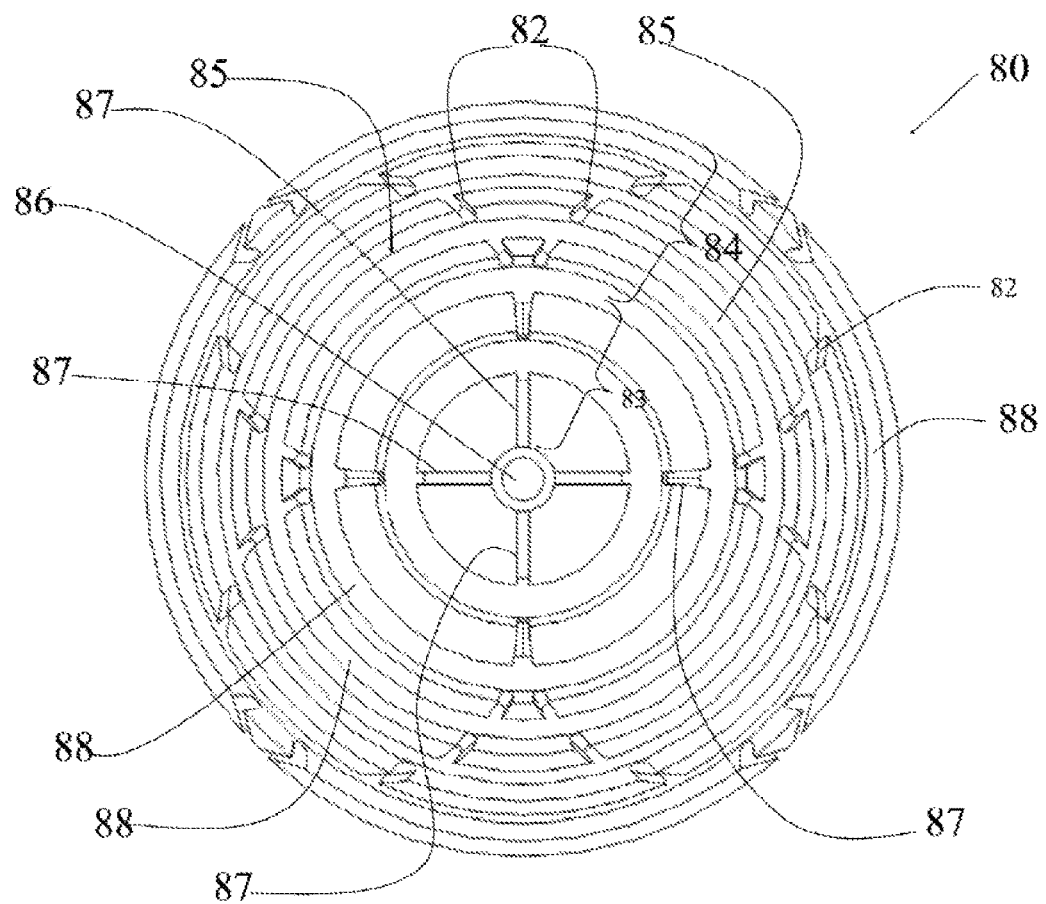

According to the invention, at least a part of the preparation of the snare is carried out on a weaving jig (block 72). FIGS. 8A and 8B show a perspective and top view, respectively, of an exemplary weaving jig 80 suitable for preparation of the retrieval snare of the present invention. The jig 80 has a structure including grooves arranged in accordance with the desired pattern of the snare of the invention and has a shape that imitates the desired shape of the snare. Specifically, the weaving jig 80 has a working surface 81, where the working surface has a predetermined convex shape defining an opening angle of the snare, and a predetermined pattern formed by radial channels 82 and concentric grooves 85 configured on the surface. The working surface 81 has a central portion 83 and a peripheral portion 84. The radial channels 82 are formed in the form of a plurality of notches extending from a center 86 of the surface towards the peripheral portion 84. The notches are not interconnected at the peripheral portion 84 of the working surface 81, but each notch merges with an adjacent notch at a shared common part 87 of the radial channels 82 in the central portion 83.

Referring to FIG. 7 and FIGS. 8A-8B together, the process for the fabrication of the retrieval snare of the present invention further includes weaving the retrieval snare on the jig 80. Specifically, the filaments are placed (block 73) into the radial channels 82 to form a plurality of filament loops in accordance with a desired pattern of the snare structure. Free parts of the filaments are arranged in the center 86 of the working surface 81 of the jig 80.

In order to avoid the filaments slipping from the jig 80 and unweaving the snare, the filament loops are fastened (block 74) to the jig at the peripheral portion 84 of the working surface of the jig. For this purpose the filaments forming the loops can be tied up on the jig 80, for example, by one or more strings (not shown in FIG. 8) wound around the jig in the concentric grooves 85. The strings can, for example, be made of soft wire having strength sufficient to maintain the fixture of the loops on the jig. Examples of the soft wire include, but are not limited to a copper wire or annealed manganin wire.

Thereafter, the process includes the step of connecting (block 75) each side of each filament loop disposed in the common part 87 of the radial channels 82 to a side of an adjacent filament loop at more than one point. According to an embodiment of the invention, the connection of the sides in the common part of the radial channels 82 is achieved by twisting each pair of the filaments forming the corresponding sides along the peripheral portion 84. In this case, the number of the connection points determines structural rigidity of the snare. This number is defined by the number of turns in the twisted portions of the loops.

Further, free parts of the filaments (not shown) arranged in the center 86 of the working surface and extended therefrom are fastened together (block 76). This fastening can, for example, be carried out by a temporal or permanent ferrule (not shown). This ferrule can, for example, be in the form of a pipe made of metal, for example, Ni, stainless steel, etc. The ferrule can be squeezed (crimped) for fixation of the filaments therein. It should be appreciated that this is only a non-limiting example of the filaments' fixation. Other techniques can also be used, for example, soldering, welding or gluing.

The process of snare fabrication further includes annealing (block 77) of the retrieval snare for memorizing and storing the snare shape and thereby imparting structural rigidity and dilatation ability to the snare. The parameters of the annealing depend on the materials of the filaments and the method of heating. For example, when such material is Nitinol, the annealing can be carried out at the temperature of about 400° C.-600° C. for about ten min. Such heat treatment relieves internal stresses in the material and provide the memorization of the basket shape. It should be understood that the time for the annealing may be shorter or longer than 10 minutes, depending on the heating technique, jig mass, etc. For example, when the treatment is carried out in a furnace, the treatment time should include the time of heating the jig.

It should be appreciated that the invention is not limited to the specific implementation of the annealing step. According to one embodiment, the heating is carried out by placing the snare mounted on the weaving jig in a furnace configured for this purpose.

According to another embodiment, the heating is carried out by passing an electric current through the filaments that in this case should be made from at least partially electrically conducting material. For example, when the material is Nitinol a current of about one to three amps applied over about two seconds to tens of seconds can be used.

After the annealing, the snare mounted on the jig is cooled (block 78). Then, the parts of the filaments tied at the peripheral portion 84 of the working surface of the jig and, if desired in the center 86, and then are unfastened (block 79); and the jig 80 is removed (block 710).

Thereafter, if the filaments at the end of the proximal portion are not bound, (as might happen when the parts of the filaments tied in the center 86 of the jig are unfastened for removal of the jig), then the free parts of the filaments at the end of the proximal portion are bound permanently together (block 711). The binding of the free parts of the filaments together can, for example, be carried out by a permanent ferrule.

According to yet another embodiment, when the retrieval snare is formed from a single length of filament, in order to place the filament in the radial channels 82 one end of the single length of filament is fixed, while the other end is put on the working surface 81 of the jig 80 and moved along the notches of the radial channels 82. The weaving of the snare continues by moving the free end away from the jig and returning it thereto as long as desired to form filament loops. After forming the loops the method repeats all the steps described above.

Furthermore, when desired, the process for fabrication of the retrieval basket can include a step of forming a manipulation member.

According to one embodiment of the invention, for the forming of a manipulation member, a certain number of filaments extending from the end of the snare proximal portion can be cut off, and the remaining wire filaments can be twisted together. In a preferred, but not required embodiment, the twisted wire filaments are then squeezed and heated for memorizing and storing the twisted form. As described above, the heating can, for example, be performed by applying an electric current across the rod. For example, when the material is Nitinol a current of about two to three amps applied over about two to five seconds can be used. It should be understood that the time and current values also depend on the filament diameter and the materials and generally may be shorter than two seconds or longer than five seconds.

According to one embodiment of the invention, the forming of the manipulation member, as shown in FIG. 4, includes the steps of providing the tube 42, cutting off one or more free parts of the filaments extended from the end 13, and axially disposing the remaining filaments within a lumen of the tube 42 along at least a portion of the tube's length. For additional stiffness, the remaining filaments can be twisted together before their disposing within the lumen of the tube 42. For facilitation of the contact between the inner surface of the tube and the filaments, the tube and the filaments can be crimped together. When desired, other binding techniques can be used, such as gluing, soldering and/or welding these filaments to the tube.

According to another embodiment of the invention, the forming of the manipulation member, as shown in FIG. 5, includes the steps of providing a tube 51, cutting off the free parts 52 of the filaments at a predetermined distance from the proximal end 13 of the loops, placing free ends 54 of the filaments obtained after the cutting into a lumen of the tube 51, and crimping together the pipe 51 and the free ends 54 of the filaments placed in the pipe 51.

According to a further embodiment of the invention, the forming of the manipulation member, as shown in FIG. 6, includes the steps of providing the rod element 61, providing the ferrule 62, cutting off all the free parts of the filaments at a predetermined distance from the proximal end 13 of the loops, and connecting the free ends 67 of the filaments obtained after cutting to the rod element 61 through the ferrule 62 that is placed around the rod element 61 and around the ends 67 of the filaments. When desired, the ferrule 62 includes a notch 64 configured for facilitation of the connection of the free ends 67 of the filaments to the rod element 61 by using at least one connecting technique selected from soldering, welding and gluing.

The method of fabrication of the retrieval snare can further include providing a dilator sheath (15 in FIG. 1A) adapted to penetrate into the body for reaching the object.

The method of fabrication of the retrieval snare can further include the steps of providing the manipulator (44 in FIG. 4; 53 in FIG. 5; 65 in FIG. 6) configured for manipulating the snare for extracting the object from the body, arranging the manipulation member (41 in FIG. 4; 50 in FIG. 5) within the dilator sheath, and connecting the manipulation member to the manipulator. The connecting of the manipulation member to the manipulator can, for example, be carried out by using a ferrule that is placed and crimped around the manipulation member and the manipulator.

From the foregoing description it should be appreciated that retrieval snares constructed in accordance with the present invention can comprise a variety of user desired shapes, number of loops, shape of the loops, types of connection of the loops in the proximal portion and types of connection of the loops to a manipulation member.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the snare of the present invention is not limited to a medical treatment of a human body. It can be successfully employed for medical treatments of animals as well. Furthermore, the device of the invention is suitable for retrieval of foreign objects from various cavities in the body systems, for example, from blood vessels, urination tract, etc.

Moreover, the present invention is not limited to fabrication of medical devices, thus the snare device of the invention can be used to extract any type of article from a wide range of inaccessible locations such as inside a pipe or tube (for example, the waste outlet of a domestic sink) or inside a chamber within a large piece of machinery which would be difficult to dismantle.

Also, it is to be understood that the phraseology and terminology employed herein are for the purpose of description and should not be regarded as limiting.

In the method claims that follow, alphabetic characters used to designate claim steps are provided for convenience only and do not imply any particular order of performing the steps.

It is important, therefore, that the scope of the invention is not construed as being limited by the illustrative embodiments set forth herein. Other variations are possible within the scope of the present invention as defined in the appended claims and their equivalents.

The invention claimed is:

1. A method for manufacturing a retrieval snare for entrapping and retaining a foreign object located in a body for its extraction therefrom, the method comprising:
   selecting a predetermined number of filaments;
   providing a weaving jig having a working surface, the working surface having a predetermined convex shape defining an opening angle of the snare and a predetermined pattern formed by radial channels configured on the surface, the working surface having a central portion and a peripheral portion, at least a part of the radial channels being formed in the form of a plurality of notches extending from a center of the surface towards the peripheral portion, the plurality of notches being not interconnected at the peripheral portion, and each radial channel includes at least one notch that shares a common part with at least one notch of an adjacent radial channel in the central portion of the working surface;
   placing the filaments into the radial channels to form a plurality of filament loops with free parts of the filaments arranged in the center of the working surface;
   fastening the filament loops to the jig at the peripheral portion of the working surface;
   connecting each side of each filament loop disposed in the common part of the radial channels to a side of an adjacent filament loop at more than one point;
   fastening the free parts of the filaments arranged in the center of the working surface together;
   shape storing annealing the retrieval snare, thereby imparting structural rigidity and dilatation ability to the snare;
   cooling the retrieval snare;
   unfastening the parts of the filaments tied at least at the peripheral portion of the working surface;
   removing the jig; and
   binding the free parts of the filaments together.

2. The method of claim 1 wherein the sides of the filament loops disposed in the common part of the radial channels are connected by twisting each pair of the filaments forming the corresponding sides.

3. The method of claim 1 further including the step of forming a manipulation member.

4. The method of claim 3 wherein the forming of the manipulation member includes twisting the free parts of the filaments.

5. The method of claim 3 wherein the forming of the manipulation member includes:
   providing a tube; and
   cutting off a predetermined number of the free parts of the filaments and axially disposing the remaining filaments within a lumen of the tube along at least a portion of a length of the tube.

6. The method of claim 1 further comprising the step of attaching at least one radiopaque marker to at least one filament loop.

7. The method of claim 3 further comprising:
   providing a sheath adapted to penetrate into the body for reaching the object;
   providing a manipulator configured for manipulating the snare for extraction the object from the body,
   arranging a manipulation member within the sheath; and
   connecting the manipulation member to the manipulator.

* * * * *